United States Patent [19]

Taylor et al.

[11] 3,989,675

[45] Nov. 2, 1976

[54] OXO PROCESS FOR PRODUCING AN ALDEHYDE

[75] Inventors: Otis C. Taylor; Lee A. Lemaster, both of Freeport, Tex.

[73] Assignee: The Dow Chemical Company, Midland, Mich.

[22] Filed: Nov. 24, 1967

[21] Appl. No.: 685,278

Related U.S. Application Data

[60] Continuation-in-part of Ser. No. 343,925, Jan. 24, 1964, abandoned, which is a division of Ser. No. 64,988, Oct. 26, 1960, abandoned.

[52] U.S. Cl. .......................................... 260/604 HF
[51] Int. Cl.² ........................................ C07C 45/02
[58] Field of Search ..................... 260/604, 604 HF

[56] References Cited
UNITED STATES PATENTS

| | | | |
|---|---|---|---|
| 2,640,074 | 5/1953 | Gresham et al. | 260/604 |
| 3,102,899 | 9/1963 | Cannell | 260/604 HF |
| 3,150,188 | 9/1964 | Eisenmann et al. | 260/598 |
| 3,274,263 | 9/1966 | Greene et al. | 260/604 X |
| 3,448,157 | 6/1969 | Slaugh et al. | 260/604 |

OTHER PUBLICATIONS

Hatch, L.F. Higher Oxo Alcohols, pp. 1 to 9, 1957.

*Primary Examiner*—James O. Thomas, Jr.
*Assistant Examiner*—W. B. Lone
*Attorney, Agent, or Firm*—Ralph M. Mellom

[57] ABSTRACT

In an Oxo process wherein an olefin, $CO_2$ and $H_2$ are reacted in the presence of a cobalt salt as catalyst, higher activity and longer useful life of the catalyst are achieved by complexing the catalyst with triphenyl phosphine.

5 Claims, No Drawings

OXO PROCESS FOR PRODUCING AN ALDEHYDE

This is a continuation-in-part of our copending application Ser. No. 343,925, filed Jan. 24, 1964, and now abandoned which in turn is a division of our copending application Ser. No. 64,988, filed Oct. 26, 1960, and now abandoned.

This invention relates to an improved Oxo process wherein an acyclic olefin, carbon monoxide and hydrogen are reacted in the presence of a cobalt catalyst to produce aldehydes.

It has now been discovered that by use of a catalyst comprising a cobalt salt complexed with triphenyl phosphine exceptionally fast reaction and high yields are obtained and the catalyst is readily recovered and reused.

According to the invention, a lower acyclic olefin, i.e., one containing up to about eight carbon atoms, is condensed with carbon monoxide and hydrogen to produce the corresponding aldehyde containing one more carbon atom than the olefin by heating the catalyst and reactants, preferably in a solvent or diluent, at a suitable temperature. Suitably the reaction is conducted at about 150° to 300° C. and a corresponding pressure of about 2000 to 5000 p.s.i., and preferably at 160° to 180° C. and 2500 to 3000 p.s.i. Reaction times are short, being usually less than 30 minutes, and preferably about 2 to 10 minutes.

boiling in the range of about 140° to 250° C., are preferred because they are most effective in keeping the catalyst in solution so that after removal of the product the catalyst can be recycled and reused. It is preferred that the solvent have a boiling point sufficiently above that of the aldehyde being produced that the latter can readily be distilled from the reaction mixture and thus leave the catalyst dissolved in the solvent. This solution can then be recycled to the reaction zone.

Practice of the invention is illustrated by the following examples.

GENERAL PROCEDURE

A 150 ml. stainless steel rocking autoclave was used as a reactor.

The catalyst was made by dissolving a cobalt salt and triphenyl phosphine in a 1:4 mole ratio in a solvent so as to have a cobalt concentration of 1% by weight in the total reaction mixture.

Into the reactor was placed 100 ml. of the catalyst solution, after which the reactor was heated to reaction temperature (160°–170° C.) and then pressurized with an equimolar mixture of carbon monoxide, hydrogen and ethylene, the three being pumped in separately in the order listed. The reactor was then agitated by rocking and the temperature was maintained constant for one hour, during which time periodic pressure readings were taken to indicate the rate of reaction. Results are shown in Table I.

TABLE I

| Ex. No. | Cobalt Salt | Triphenyl Phosphine | Solvent[a] | Pressure (p.s.i.) During Reaction Period Reaction Time, Min. | | | | | | | | |
|---|---|---|---|---|---|---|---|---|---|---|---|---|
| | | | | 0 | 2 | 4 | 6 | 8 | 10 | 20 | 30 | 60 |
| 1 | Naphthenate | no | Dowtherm A | 2500 | 2450 | 2400 | 2350 | 2300 | 2250 | 2250 | 2225 | 2225 |
| 2 | '' | yes | '' | 2500 | 2000 | 1300 | 1175 | 1150 | 1150 | 1125 | 1100 | 1050 |
| 3 | '' | no | TTCM | 2500 | 2500 | 2500 | 2500 | 2500 | 2500 | 2375 | 2375 | 2350 |
| 4 | '' | yes | '' | 2500 | 1500 | 700 | 600 | 600 | 550 | 550 | 550 | 550 |
| 5 | '' | yes | AMN | 2500 | 2275 | 2175 | 2050 | 2000 | 1950 | 1300 | 650 | 650 |
| 6 | '' | yes | MP | 2500 | 2300 | 750 | 550 | 550 | 550 | 525 | 525 | 525 |
| 7 | '' | yes | DMF | 2500 | 2175 | 750 | 625 | 600 | 575 | 575 | 575 | 575 |
| 8 | '' | yes | Propionic acid | 2500 | 2280 | 2320 | 2320 | 2350 | 2360 | 1980 | 1320 | 820 |
| 9 | '' | no | '' | 2500 | 2000 | 2050 | 2050 | 2025 | 2000 | 2025 | 2035 | 2000 |
| 10 | Octoate | no | '' | 2500 | 2130 | 2130 | 2130 | 2130 | 2130 | 2130 | 2120 | 2100 |
| 11 | '' | yes | Toluene | 2500 | 2030 | 1960 | 1875 | 1810 | 1730 | 500 | 500 | 500 |
| 12 | '' | yes | AMN | 2500 | 2215 | 2140 | 2090 | 1770 | 1590 | 850 | 670 | 550 |
| 13 | Bromide | yes | Dowtherm | 2475 | 2250 | 2050 | 1450 | 1000 | 900 | 775 | 750 | 750 |
| 14 | '' | yes | TTGM | 2500 | 2200 | 2000 | 1750 | 1600 | 1410 | 675 | 575 | 550 |
| 15 | Bromide | yes | Propionic acid | 2500 | 2300 | 2250 | 2180 | 2020 | 1850 | 650 | 650 | 600 |
| 16 | Acetate | yes | Water | 2500 | 2475 | 2450 | 2375 | 2375 | 2300 | 2050 | 1750 | 865 |
| 17 | '' | yes | Propionic acid | 2500 | 2250 | 1850 | 1750 | 1640 | 1520 | 1000 | 785 | 700 |
| 18 | '' | yes | DMF | 2500 | 850 | 725 | 675 | 675 | 650 | 600 | 600 | 600 |
| 19 | '' | yes | MP | 2500 | 1450 | 800 | 600 | 575 | 550 | 525 | 525 | 525 |

[a]Dowtherm A is a eutectic mixture of diphenyl and diphenyl ether.
TTCM is tetraethylene glycol dimethyl ether.
AMN is alpha-methylnaphthalene.
MP is N-methyl-2-pyrrolidone.
DMF is dimethyl formamide.

The catalyst of the invention is a complex of a cobalt salt with triphenyl phosphine. Being solid, such catalyst must be dissolved in a solvent to be effective. The olefin reactant can serve as the solvent provided the catalyst is adequately soluble therein. Olefins containing four or more carbon atoms readily dissolve many cobalt salt complexes with triphenyl phosphine, and thus serve admirably as solvents. When using the olefins containing less than four carbon atoms it is usually preferable to use another solvent. Among the suitable solvents are diphenyl ether, toluene, aliphatic ethers, N-methyl pyrrolidone, dimethyl formamide and the lower alkanoic acids. The latter, particularly those In the above examples, a 4:1 molar ratio of triphenyl phosphine to cobalt salt was used. However, such a large ratio is not necessary. A 1:1 ratio is effective, although it is preferred to use at least 2:1 or even 3:1. On the other hand, ratios exceeding about 5:1 show little or no improvement over 3:1 or 4:1 and therefore are not commercially practical although they are operable and within the scope of the present invention.

The pressure drop in the above examples is a direct measure of the extent of reaction, the product in all cases being propionaldehyde. In many of the experiments the product was isolated by cooling the reactor, venting the residual gases through an efficient condenser and then distilling the propionaldehyde. The residue thus obtained consisted of a solution of the catalyst in the solvent and could be reused indefinitely.

The process is especially suitable for continuous operation. In one manner of so operating, the reactor is an upright packed column into which the catalyst solution is fed at the top and the reactants are fed in near the bottom. From the bottom is drawn a liquid stream which is passed through two or more stripping towers in which unused reactants and the product are removed, after which the catalyst-solvent mixture is recycled to the reactor.

Although the above examples utilize ethylene as the olefin, any other acyclic olefin useful in the Oxo process can be used instead of ethylene, thus producing the corresponding aldehydes. Suitable olefins include propylene, 1,2-butylene, n-butylene, isobutylene, pentenes, diolefin, e.g. butadiene and aryl substituted olefins, e.g. styrene.

Any cobalt salt may be used as the cobalt catalyst. It is preferred to use those which require no special solubilization. Among the more practical ones are the chloride, bromide, iodide, acetate, propionate, octoate, benzoate, lactate, sulfate, nitrate and the like.

We claim:

1. In a process wherein a lower acyclic olefin, carbon monoxide and hydrogen are reacted in the presence of a cobalt salt to produce an aldehyde, the improvement comprising using as a catalyst a complex of cobalt salt with at least an equimolar amount of triphenyl phosphine, said process being conducted at a temperature of about 150° to 300° C. and a pressure of about 2000 to 5000 p.s.i.

2. A process as defined in claim 1 wherein the salt and the phosphine are dissolved in an alkanoic acid of boiling point not higher than 250° C.

3. A process as defined in claim 2 wherein the alkanoic acid has a boiling point of about 140° to 250° C.

4. A process as defined in claim 2 wherein the acid is propionic acid.

5. In a process for making propionaldehyde by the reaction of ethylene, carbon monoxide and hydrogen in the presence of a cobalt catalyst and at a temperature of about 150° to 300° C. and a pressure of about 2000 to 5000 p.s.i., the improvement comprising using as the catalyst a solution in propionic acid of cobalt propionate and at least about an equimolar amount, based on the cobalt, of triphenyl phosphine.

* * * * *